United States Patent
Iannone et al.

(10) Patent No.: US 10,046,321 B2
(45) Date of Patent: Aug. 14, 2018

(54) DIAGNOSTIC DEVICE, PARTICULARLY OF THE LAB-ON-CHIP TYPE

(71) Applicant: Eugenio Iannone, Milan (IT)

(72) Inventors: Eugenio Iannone, Milan (IT); Maurizio Moroni, Milan (IT); Giacomo Germani, Buccinasco (IT)

(73) Assignee: DIANAX S.R.L., Milan (IT)

( * ) Notice: Subject to any disclaimer, the term of this patent is extended or adjusted under 35 U.S.C. 154(b) by 109 days.

(21) Appl. No.: 15/022,746

(22) PCT Filed: Sep. 16, 2014

(86) PCT No.: PCT/EP2014/069668
§ 371 (c)(1),
(2) Date: Mar. 17, 2016

(87) PCT Pub. No.: WO2015/040009
PCT Pub. Date: Mar. 26, 2015

(65) Prior Publication Data
US 2016/0207043 A1  Jul. 21, 2016

(30) Foreign Application Priority Data

Sep. 19, 2013 (IT) .............................. MI2013A1541

(51) Int. Cl.
*G01N 27/453* (2006.01)
*B01L 3/00* (2006.01)
*G01N 27/447* (2006.01)

(52) U.S. Cl.
CPC ..... *B01L 3/502715* (2013.01); *B01L 3/50273* (2013.01); *B01L 3/502738* (2013.01);
(Continued)

(58) Field of Classification Search
CPC .................... G01N 27/44791; C12N 15/101
See application file for complete search history.

(56) References Cited

U.S. PATENT DOCUMENTS

| 5,922,591 A | 7/1999 | Anderson et al. |
| 2004/0265172 A1* | 12/2004 | Pugia ............... B01L 3/502746 |
| | | 422/400 |

(Continued)

FOREIGN PATENT DOCUMENTS

| WO | 9853311 A2 | 11/1998 |
| WO | WO 03/011768 A2 * | 2/2003 ............... C02F 1/40 |

(Continued)

OTHER PUBLICATIONS

International Search Report dated Nov. 25, 2014 re: Application No. PCT/EP2014/069668; pp. 1-4; citing: WO 2010/009415 A1, Briani et al., WO 2012/111429 A1, WO 98/53311 A2 and US 5 922 591 A.
(Continued)

*Primary Examiner* — Alexander S Noguerola
(74) *Attorney, Agent, or Firm* — Cantor Colburn LLP (57) ABSTRACT

A diagnostic device, particularly of the lab-on-chip type having
a station for inserting a native sample of a fluid to be tested;
a chamber for stabilizing the native sample,
and a station for separating the native sample.
The device further includes an electrophoresis chamber, with a capillary connection to the separation station,
a reaction chamber, and
at least one pair of electrodes. The electrodes are arranged upstream and downstream of the electrophoresis chamber, whose electrical field propels the sample from the electrophoresis chamber to the reaction chamber, a separative electrophoresis occurring inside the electrophoresis chamber. The insertion station, the stabilization chamber, the separation station, the electrophoresis chamber (5) and the reaction chamber are defined in a single chip and include inert containment surfaces.

8 Claims, 7 Drawing Sheets

(52) U.S. Cl.
CPC .. B01L 3/502753 (2013.01); G01N 27/44791 (2013.01); B01L 2200/027 (2013.01); B01L 2200/0684 (2013.01); B01L 2200/10 (2013.01); B01L 2200/141 (2013.01); B01L 2200/16 (2013.01); B01L 2300/0627 (2013.01); B01L 2300/0681 (2013.01); B01L 2300/0816 (2013.01); B01L 2300/0838 (2013.01); B01L 2300/0867 (2013.01); B01L 2300/0877 (2013.01); B01L 2400/0406 (2013.01); B01L 2400/0421 (2013.01); B01L 2400/0688 (2013.01)

(56) References Cited

U.S. PATENT DOCUMENTS

2006/0207891 A1* 9/2006 Althaus ............... C12Q 1/6825 205/787
2012/0196767 A1* 8/2012 Cooney ............. B01L 3/502715 506/9

FOREIGN PATENT DOCUMENTS

| WO | 2010009415 A1 | 1/2010 | |
|---|---|---|---|
| WO | WO 2011/156851 A1 * | 12/2011 | ............... B01L 3/00 |
| WO | 2012111429 A1 | 8/2012 | |

OTHER PUBLICATIONS

Maya Briani et al. "Design and Optimization of Reaction Chamber and Detection System in Dynamic Labs-on-Chip for Proteins Detection"; IEEE Transactions on Biomedical Engineering, Aug. 1, 2013, vol. 60, No. 8, pp. 2161-2166.

Written Opinion dated Nov. 25, 2014 re: Application No. PCT/EP2014/069668; pp. 1-4; citing: WO 2010/009415 A1, Briani et al., WO 2012/111429 A1, WO 98/53311 A2 and US 5 922 591 A.

* cited by examiner

DIAGNOSTIC DEVICE, PARTICULARLY OF THE LAB-ON-CHIP TYPE

TECHNICAL FIELD

The present disclosure relates to a diagnostic device, particularly of the lab-on-chip type.

BACKGROUND

At present, it is possible to find diagnostic devices in many and varied fields of interest, ranging for example from the industrial and food sectors to the fields of clinical diagnosis and biomedical research, and in particular in immunology, pharmacology or biochemistry.

Among such conventional diagnostic devices it is possible to cite commercially available devices, such as the bench-top analyzers sold under the names "Reflotron Plus" or "VereMTB™".

However, conventional diagnostic devices are not devoid of drawbacks, among which is the fact that often they are difficult and delicate to manage.

Another drawback of such conventional devices relates to the fact that their sensitive parts are difficult to preserve while maintaining their unalterability over time.

A drawback of such conventional diagnostic devices is that the native sample, for example blood, taken from the patient, needs to undergo vital preliminary treatments before it can be introduced into the diagnostic device in order to be analyzed. Such preliminary treatments involve direct contact with the material to be analyzed by laboratory technicians, with the risk that the material to be analyzed in such devices can be subjected to external contamination, which thus require the diagnosis tests to be repeated, with consequent increase in the associated costs.

An additional drawback of such conventional diagnostic devices is that carrying out the diagnosis is often lengthy and laborious, in that it requires, once the material to be analyzed has been gathered, for example by way of taking blood samples, many intermediate steps and much external handling.

SUMMARY

The present disclosure provides a diagnostic device, particularly of the lab-on-chip type, which eliminates the drawbacks and overcomes the limitations of the known art, by ensuring a greater and better manageability of use, as well as a longer-lasting preservability of its sensitive and/or deteriorable parts.

Within this aim, the present disclosure provides a diagnostic device that ensures the preservability and unalterability of the sample and of the reference reagent solution.

The disclosure further provides a diagnostic device that can provide diagnostic procedures that are highly accurate and repeatable, as well as fast to carry out.

The disclosure also provides a diagnostic device that requires a minimum of manipulation from the operator, thus also minimizing the risks of contamination and human error.

Still, the disclosure provides a diagnostic device that is capable of offering the widest guarantees of reliability and safety in use.

The disclosure further provides a device that is extremely versatile with respect to conventional devices, which often are specific to determined target uses.

The disclosure also provides a diagnostic device that is easy to implement and economically competitive when compared to the known art.

These benefits which will become better apparent hereinafter are achieved by a diagnostic device, particularly of the lab-on-chip type, wherein the device comprises:

a station for inserting a native sample of a fluid to be tested;

a chamber for stabilizing said native sample, directly connected to said insertion station;

a station for separating said native sample, with a capillary connection to said stabilization chamber;

an electrophoresis chamber, with a capillary connection to said separation station;

a reaction chamber, at least one pair of electrodes which are arranged upstream and downstream of said electrophoresis chamber, the electrical field generated by said pair of electrodes propelling said sample from said electrophoresis chamber to said reaction chamber, a separative electrophoresis occurring inside said electrophoresis chamber;

said insertion station, said stabilization chamber, said separation station, said electrophoresis chamber and said reaction chamber being defined in a single chip and comprising inert containment surfaces, said diagnostic device comprising a blank solution chamber, adapted to contain a blank solution, said blank solution chamber being connected to said reaction chamber by way of a first valve.

BRIEF DESCRIPTION OF THE DRAWINGS

Further characteristics and advantages of the disclosure will become better apparent from the detailed description of a preferred, but not exclusive, embodiment of a diagnostic device, particularly of the lab-on-chip type, which is illustrated for the purposes of non-limiting example with the assistance of the accompanying drawings wherein.

DETAILED DESCRIPTION OF THE DRAWINGS

With reference to the figures, the diagnostic device, particularly of the lab-on-chip type, is generally designated by the reference numeral 1.

Figure 1:
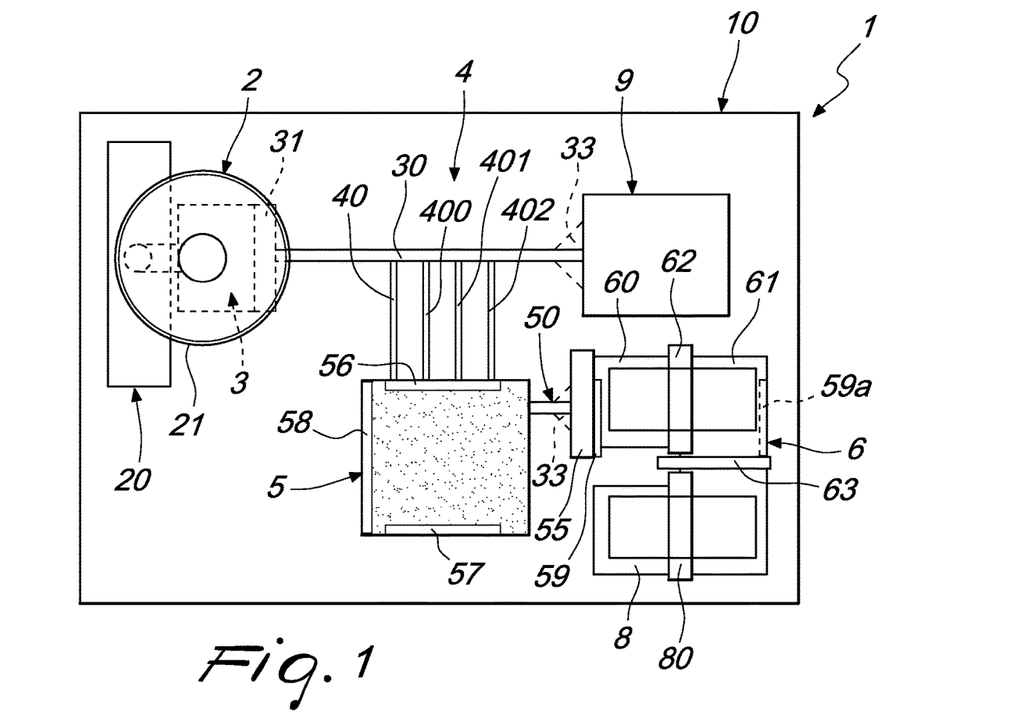
FIG. 1 is a schematic diagram of an embodiment of a diagnostic device, particularly of the lab-on-chip type, according to the disclosure.

According to the disclosure, the diagnostic device 1 comprises:
- a station 2 for inserting a native sample of a fluid to be tested;
- a chamber 3 for stabilizing the native sample, directly connected to the insertion station 2;
- a station 4 for separating the native sample, with a capillary connection to the stabilization chamber 3;
- an electrophoresis chamber 5, with a capillary connection to the separation station 4;
- a reaction chamber 6;
- at least one pair of electrodes 58, 59 which are arranged upstream and downstream of the electrophoresis chamber 5, whose electrical field propels the sample from the electrophoresis chamber 5 to the reaction chamber 6. The separative electrophoresis of the target occurs in the electrophoresis chamber 5.

According to the disclosure, furthermore, the insertion station 2, the stabilization chamber 3, the separation station 4, the electrophoresis chamber 5 and the reaction chamber 6 are defined in a single chip 10 and have inert containment surfaces, i.e. surfaces that are chemically and/or physically non-activated, i.e. surfaces that have not undergone particular processing to render them chemically and/or physically reactive.

According to the disclosure, the sample of fluid to be tested is a native sample, i.e. a sample of fluid that has been taken from the patient and which has not undergone preliminary treatments before being inserted into the insertion station 2 of the diagnostic device 1.

According to the disclosure, furthermore, in the diagnostic device 1 a blank solution chamber 8 is comprised which is adapted to contain a blank solution, for conducting parallel blank tests, so as to verify the correct operation of the test system and of the solutions used, i.e. in order to assess in real time the effective functionality and activity of the reagent present in the reagent solution used for detection. The blank test is in fact produced by duplicating the reaction chamber 6 and substituting the solution of the sample to be analyzed with a suitable blank. The blank solution chamber 8 is in fact connected with the reaction chamber 6 by way of a first valve 80.

The blank solution chamber 8 is advantageously arranged in the chip 10 in a region that is some distance from the reaction chamber 6.

The diagnostic device 1 is particularly adapted for the detection of targets of biomedical interest, such as proteins of various types, in physiological fluids, such as blood, urine, saliva, by way of immunological tests or direct detection. Advantageously the diagnostic device 1 is also adapted to be applied in the food industry sector, where liquids such as milk and wine can be analyzed in order to determine their quality, sophistication and presence of any harmful substances. Also, advantageously the diagnostic device 1 is also adapted to be applied in the veterinary and animal management sector where fluids of an animal nature can be analyzed for the purpose of diagnosis, monitoring of the development of diseases and the progress of treatments.

Advantageously, in addition to the pair of electrodes 58, 59 that are arranged upstream and downstream of the electrophoresis chamber 5, and which define an electrical field that propels the sample from the electrophoresis chamber 5 to the reaction chamber 6, there is a second pair of electrodes 56, 57, which are adapted to generate an electrical field that is perpendicular to the electrical field generated by the electrodes 58, 59, thus making it possible to obtain a two-dimensional electrophoresis. Such solution of two-dimensional electrophoresis is particularly useful for complex samples and samples that are rich in impurities, or for targets that travel accompanied by similar molecules and which thus would not be effectively separable using a normal one-dimensional electrophoresis.

Figure 2:
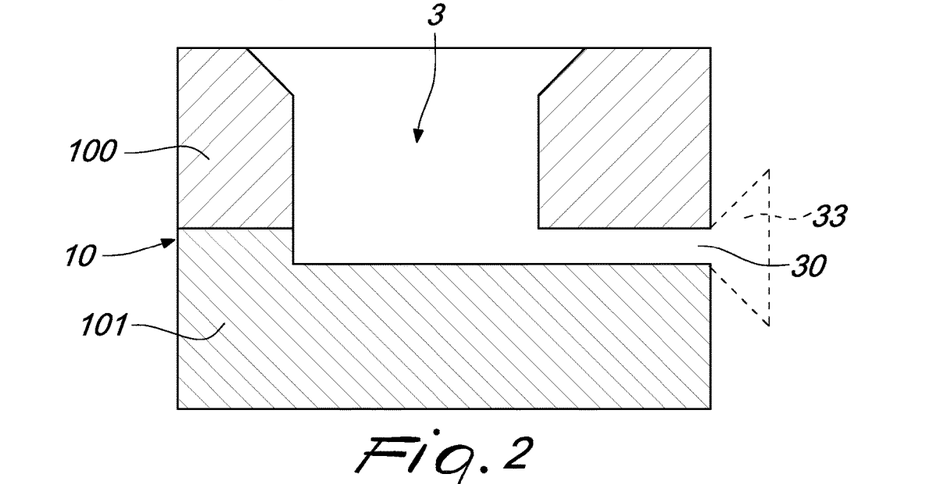
FIG. 2 is a cross-sectional side view of a part of the diagnostic device in FIG. 1, illustrating in particular the stabilization chamber.

FIG. 2 illustrates in particular the portion of the chip 10 where the stabilization chamber 3 is provided. The stabilization chamber 3 is made with optimized specifications for the mixing of the sample to be tested with a stabilization solution, so as to prepare it for the subsequent processes. The stabilization solution advantageously contains all the components necessary in order to prevent side effects that would render the tests impossible, such as for example pH aberrations, coagulation of the blood, or unwanted precipitations. Stabilization of the sample to be tested is particularly necessary for samples that can, in the short term, experience biochemical modifications that would make it no longer possible to analyze them or which would lead to the degradation of the sought target. For example, with blood, coagulation has to be prevented and also the false positives generated by bivalent cations, and therefore the stabilization solution will have to contain both anticoagulants and adapted chelating agents. The type of stabilization solution is thus strictly linked to the nature of the sample to be analyzed and to the sought target.

The quantity of sample to be tested is generally of the order of a microliter, and the stabilization solution is adapted to dilute the sample by values of around 50%.

The dimensions of the stabilization chamber 3 are advantageously 1 mm×1 mm×0.2 mm. Given that the stabilization solution is added directly in the stabilization chamber 3, in order to prevent the outflow thereof during the manipulation or storage of the chip 10, the stabilization chamber 3 is advantageously closeable, for example with a layer of removable adhesive material.

Figure 7:
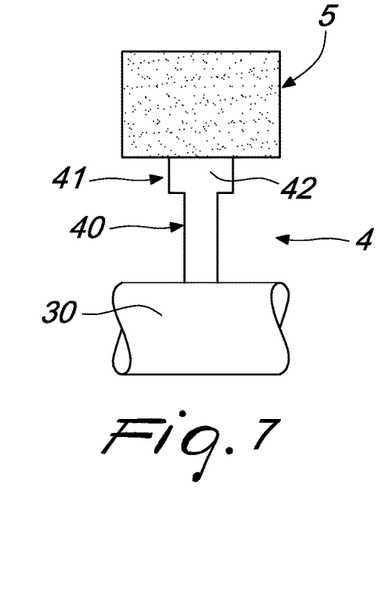
FIG. 7 is a view from above of a part of the diagnostic device in FIG. 1, illustrating in particular a capillary duct of the separation station.
Figure 8:
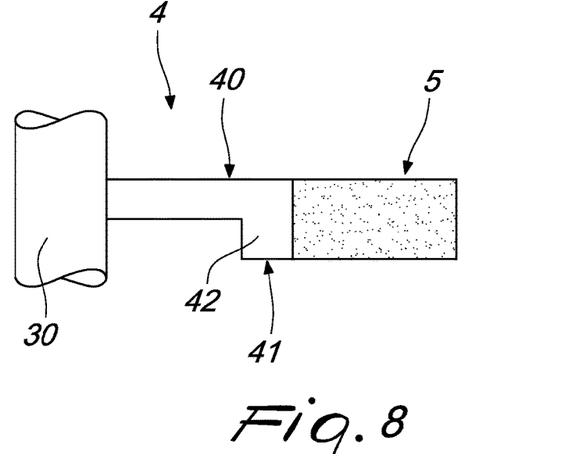
FIG. 8 is a cross-sectional side view of the diagnostic device part shown in FIG. 7.

The separation station 4 advantageously comprises a main capillary duct 30 and at least one lateral capillary duct 40 that branches off from the main capillary duct 30. The opening of the lateral capillary duct 40 has a cross-section that is substantially smaller than the cross-section of the opening of the main capillary duct 30. In this manner, the sample, in passing by capillary action between the main capillary duct 30, and the lateral capillary ducts 40, 400, 401, 402, is separated from unwanted larger accompanying particles, in this manner obtaining a first filtration by separation.

The separation that occurs in the separation station 4 is based on the dependency of the diffusion coefficient on the molecular mass so as to optimize the molarity of the sought target in the final solution.

Figure 6:
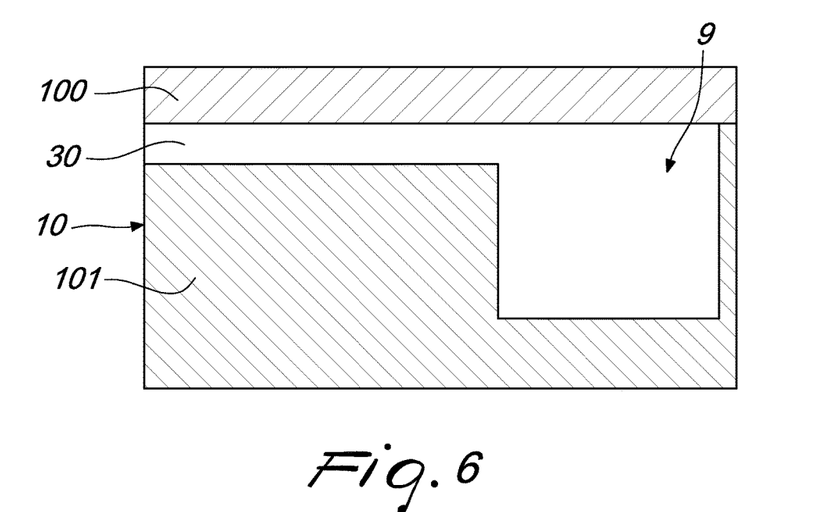
FIG. 6 is a cross-sectional side view of a part of the diagnostic device in FIG. 1, illustrating in particular the discharge chamber.

The stabilization chamber 3 is advantageously connected by way of the main capillary duct 30 to the discharge chamber 9, as illustrated in FIG. 6.

The stabilization chamber 3 is advantageously separated from such main capillary duct 30 by way of an opening valve 31.

Figure 3:
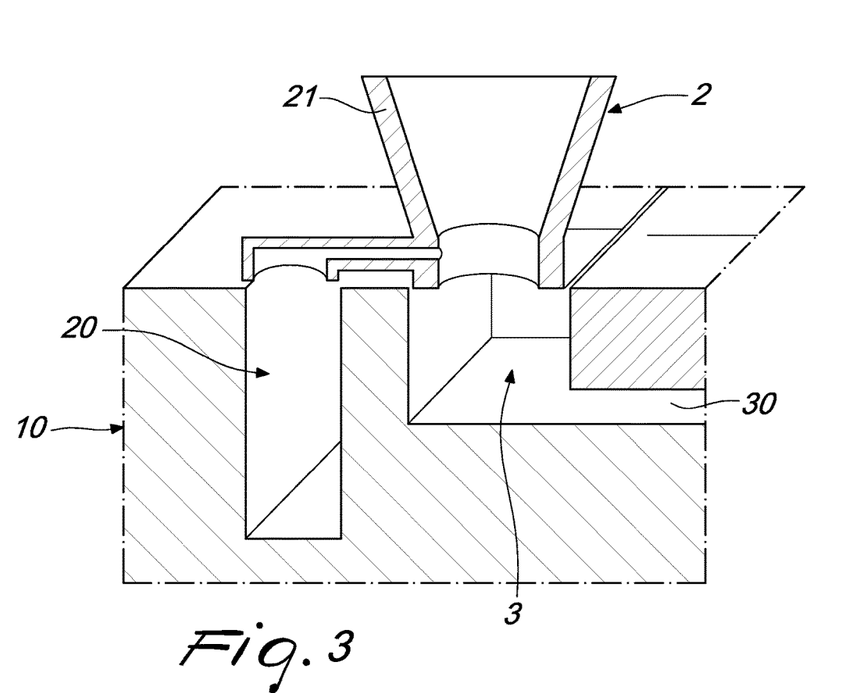
FIG. 3 is a cross-sectional perspective view of a first variation of the stabilization chamber shown in FIG. 2, which also has an overflow chamber.

The discharge chamber 9 is adapted to collect the waste part of the sample, which is filtered by the separation station 4, and which therefore does not continue on the path to the electrophoresis chamber 5. Such waste part comprises cells, and other unfiltered materials, as well as the air compressed by loading the sample into the stabilization chamber 3, which in fact has one escape route, through the main capillary duct 30, into the discharge chamber 9, such air in fact having no other exit routes in the chip 10. In fact the discharge chamber 9 is made so as to maintain the correct air/fluid interface in the main capillary duct 30 thus ensuring the movement by capillary action thereof. Advantageously, the volume of the discharge chamber 9 is at least double the sum of the volumes of the stabilization chamber 3 and of the main capillary duct 30, precisely in order to maintain the capillary flow at a constant pressure, as the volume of sample decreases in level in the stabilization chamber 3. For this reason, as illustrated in FIG. 3, the main capillary duct 30 leads into the discharge chamber 9 in its upper part. The discharge chamber 9 has advantageously dimensions in the order of 1 mm×1.5 mm×0.2 mm, and is thus sufficiently large to avoid obstructions owing to the depositing of cells on the walls thereof.

Advantageously, the lateral capillary duct 40, which extends longitudinally, comprises at least one longitudinal portion 41 that has a transverse cross-section of greater area than the transverse cross-section of the remaining longitudinal portion of the lateral capillary duct 40, so that the longitudinal portion 41, having a transverse cross-section of greater area, defines a first expansion volume 42.

Preferably there is a plurality of first capillary ducts 40, 400, 401, 402, all of which advantageously have an expansion volume. Through such capillary ducts the air is compressed between the fluid that advances by capillary action and the gel present in the electrophoresis chamber 5. In order to allow the penetration of the sample into the gel, it is necessary to prevent a gaseous interface from remaining between the gel and the sample, instead maintaining a liquid interface in order to stimulate the effect of diffusion in the gel. The first expansion volume 42 is adapted to accommodate the air that is propelled by the sample into the passage through the lateral capillary duct 40.

Figure 10:
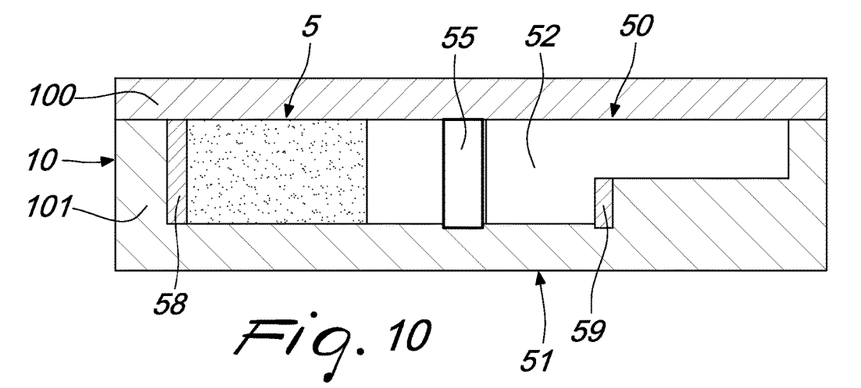
FIG. 10 is a cross-sectional side view of a part of the diagnostic device in FIG. 1, illustrating in particular the electrophoresis chamber and the capillary duct that connects it with the reaction chamber.

Advantageously, comprised between the electrophoresis chamber 5 and the reaction chamber 6 is a second capillary duct 50 that is extended longitudinally and comprises at least one longitudinal portion 51 that has a transverse cross-section of greater area than the transverse cross-section of the remaining longitudinal portion of the second capillary duct 50, so that the longitudinal portion 51, having a transverse cross-section of greater area, defines a second expansion volume 52.

Such second expansion volume is advantageously filled with a saline solution with a pH value that is geared to maintain the target, now purified of inconvenient accompanying particles, in solution and at the correct concentration for the subsequent step of detection. The outflow of the target from the electrophoresis chamber 5, and its consequent entry into the second expansion volume 52 which is filled with saline solution, is achieved by the application of an electrical field that is perpendicular to the separative electrophoresis electrical field. Such electrical field is provided by the pair of electrodes 58, 59 which are arranged upstream and downstream of the electrophoresis chamber 5. In particular, FIGS. 1 and 10 illustrate a first electrode 58 which is arranged upstream of the electrophoresis chamber 5, and a second electrode 59 which is arranged in the second capillary duct 50 upstream of the electrophoresis chamber 5, and in particular upstream of the second expansion volume 52 containing the saline solution. The activation of the pair of electrodes 58, 59 entails the expulsion of the target from the electrophoresis chamber 5 toward the reaction chamber 6.

The existence of the second capillary duct 50 between the electrophoresis chamber 5 and the reaction chamber 6 has the twofold role of selecting the target from other possibilities by opening the minimum amount of space necessary to capture the appropriate electrophoretic line, and at the same time to enable the positioning of a shut-off valve 55, which is adapted to separate the reaction chamber 6 from the electrophoresis chamber 5.

Advantageously the pair of electrodes 58, 59 can be arranged according to alternative configurations, as long as they are arranged upstream and downstream of the electrophoresis chamber 5. In particular, the second electrode 59 can be arranged directly adjacent to, for example, the shut-off valve 55 of the reaction chamber 6, or inside said reaction chamber 6. FIG. 1 shows, with a dotted line, the position 59a of the electrode arranged inside the reaction chamber instead of adjacent to the shut-off valve 55. If the electrode 59 is arranged adjacent to the shut-off valve 55, and thus upstream of the reaction chamber 6, the electrode 59 is conveniently pierced or notched in order to allow the proteic fluid to pass through when the shut-off valve 55 is opened.

Figure 9:
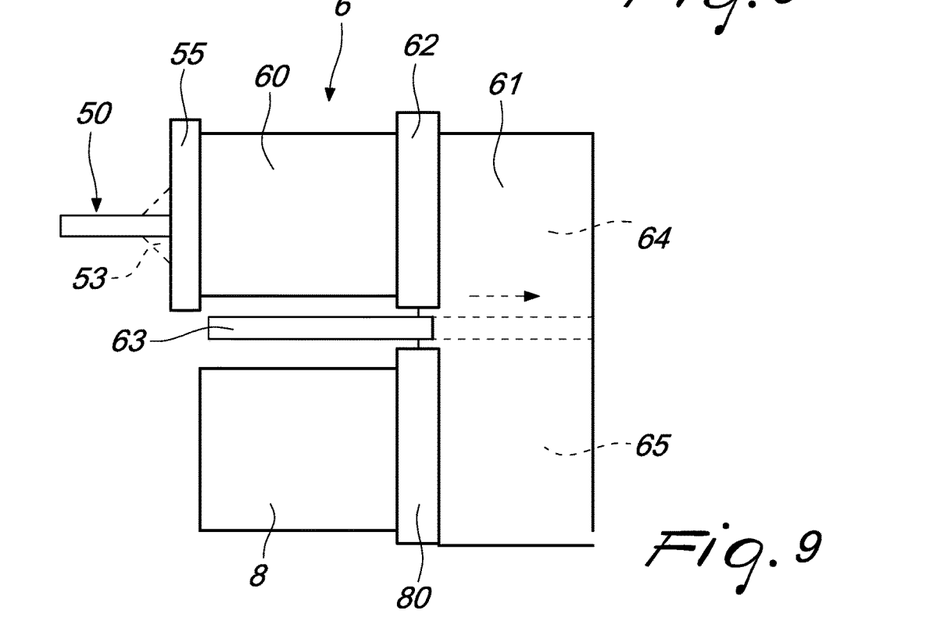
FIG. 9 is a view from above of a part of the diagnostic device in FIG. 1, illustrating in particular an embodiment of the reaction chamber.

The reaction chamber 6 can advantageously comprise a first chamber 60, adapted to accommodate the solution to be tested, and a second chamber 61, adapted to contain a reagent solution. The first chamber 60 and the second chamber 61 are separated by a second valve 62.

According to a preferred embodiment of the reaction chamber 6, shown in FIG. 9, the reaction chamber 6 includes both the structures necessary for the detection test and the structures necessary for the blank test. In particular, the reaction chamber 6 directly comprises the blank solution chamber 8; the reaction chamber 6 comprises a third valve 63 adapted to separate the second chamber 61 into two sub-chambers 64, 65, where the first sub-chamber 64 is connected with the first chamber 60 by way of the second valve 62, and the second sub-chamber 65 is connected with the blank solution chamber 8 by way of the first valve 80.

Advantageously, the diagnostic device 1 comprises an overflow chamber 20 adapted to collect the excess sample that exits from the stabilization chamber 3, as illustrated in FIG. 3. The existence of an overflow chamber 20 is particularly useful when the sample to be analyzed is related to infectious diseases and/or chemically hazardous activities.

Figure 4:
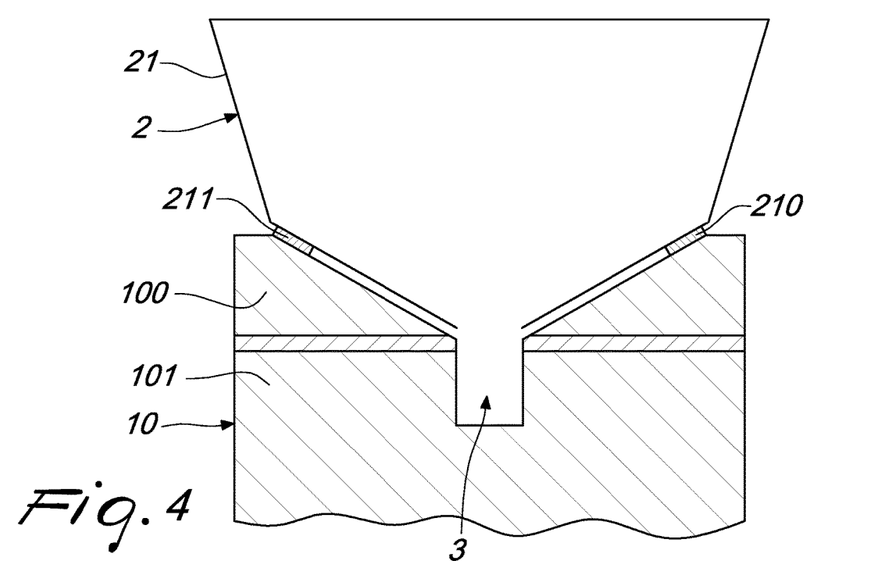
FIG. 4 is a cross-sectional side view of a part of the diagnostic device in FIG. 1, illustrating in particular the insertion station.

Furthermore, in the diagnostic device 1, the insertion station 2 advantageously comprises a funnel-like element 21, illustrated in FIGS. 3 and 4. The funnel-like element 21 can be advantageously made of an adapted polymeric material, such as for example of the type of PMDS or SU8, by way of micro-molding or hot-embossing techniques, and can be fixed at adapted fixing points 210, 211, by way of laser-welding techniques.

Figure 5:
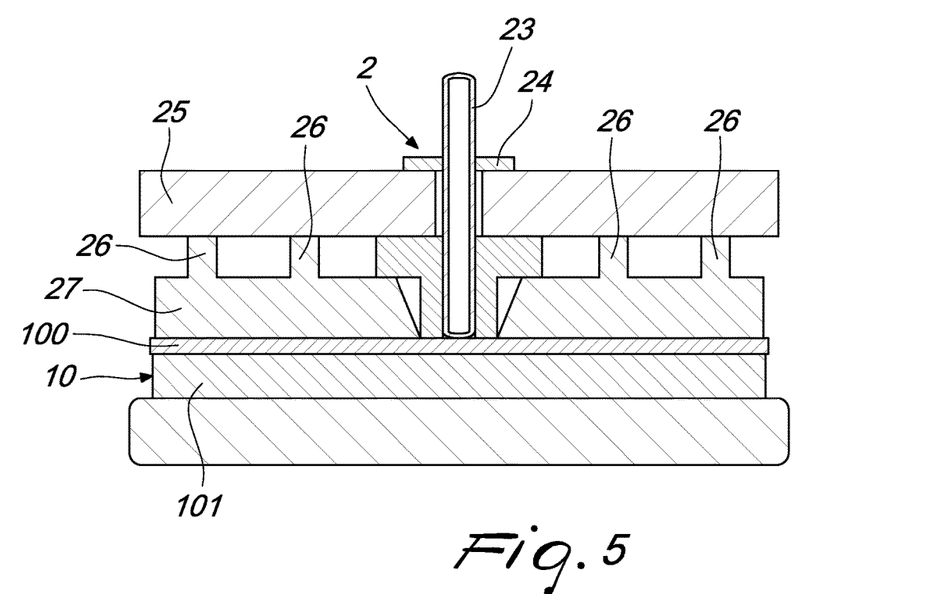
FIG. 5 is a cross-sectional side view of a part of the diagnostic device in FIG. 1, illustrating in particular a variation of the insertion station shown in FIG. 4.

FIG. 5 illustrates an alternative embodiment of the insertion station 2, which involves the use of a capillary tube 23, fixed by way of a gasket 24, of the O-ring type, to a structure 25 that covers the chip 10 and is conveniently connected thereto by way of adapted spacers 26 that are formed by and protrude from a layer 27 of vitreous material.

The diagnostic device 1 comprises various valves 31, 55, 62, 63, 80.

Figure 11:
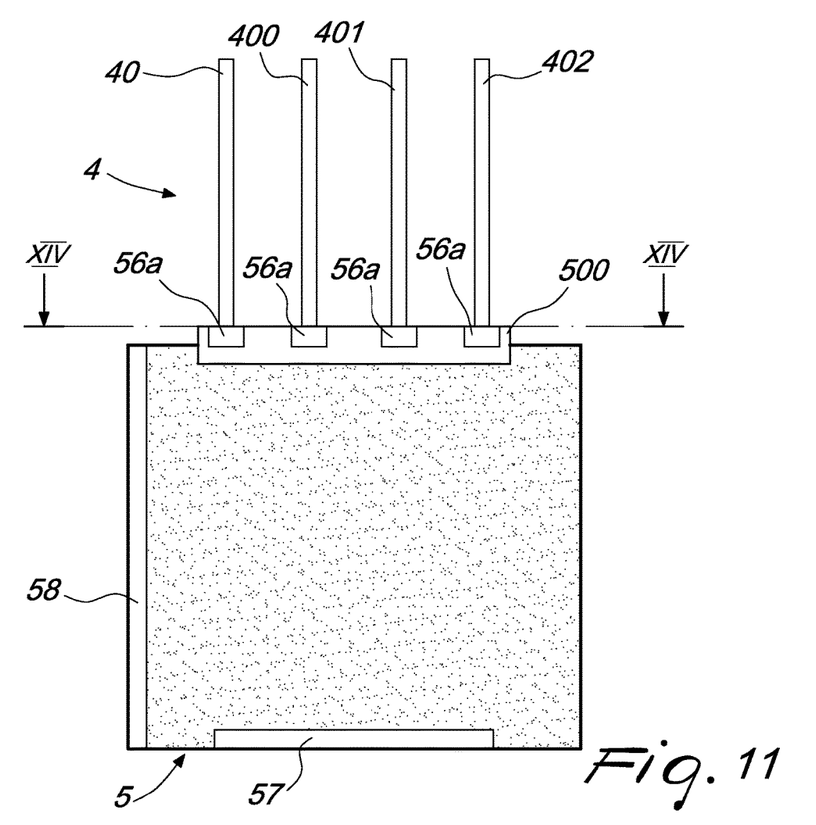
FIG. 11 is a view from above of a part of the diagnostic device in FIG. 1, illustrating in particular a first variation of the interface between the separation station and the electrophoresis chamber.
Figure 12:
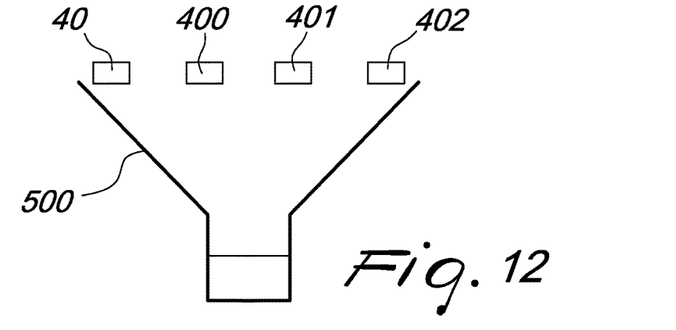
FIG. 12 is a cross-sectional side view of the portion of interface shown in FIG. 11, taken along the line XIV-XIV.

FIGS. 11 and 12 illustrate a first variation of the interface between the filtration station 4 and the electrophoresis chamber 5. The first ducts 40, 400, 401, 402 convey the sample to a collection well 500, in the shape of a funnel. In this manner the filtered sample can be moved as a single mass inside the gel of the electrophoresis chamber 5, by way of the electrical fields generated by the electrodes 56, 57, 58, 59. Furthermore, the electrode 56 can be defined by a plurality of smaller electrodes 56a, which are mutually connected and are arranged at each of the first ducts 40, 400, 401, 402.

Figure 13:
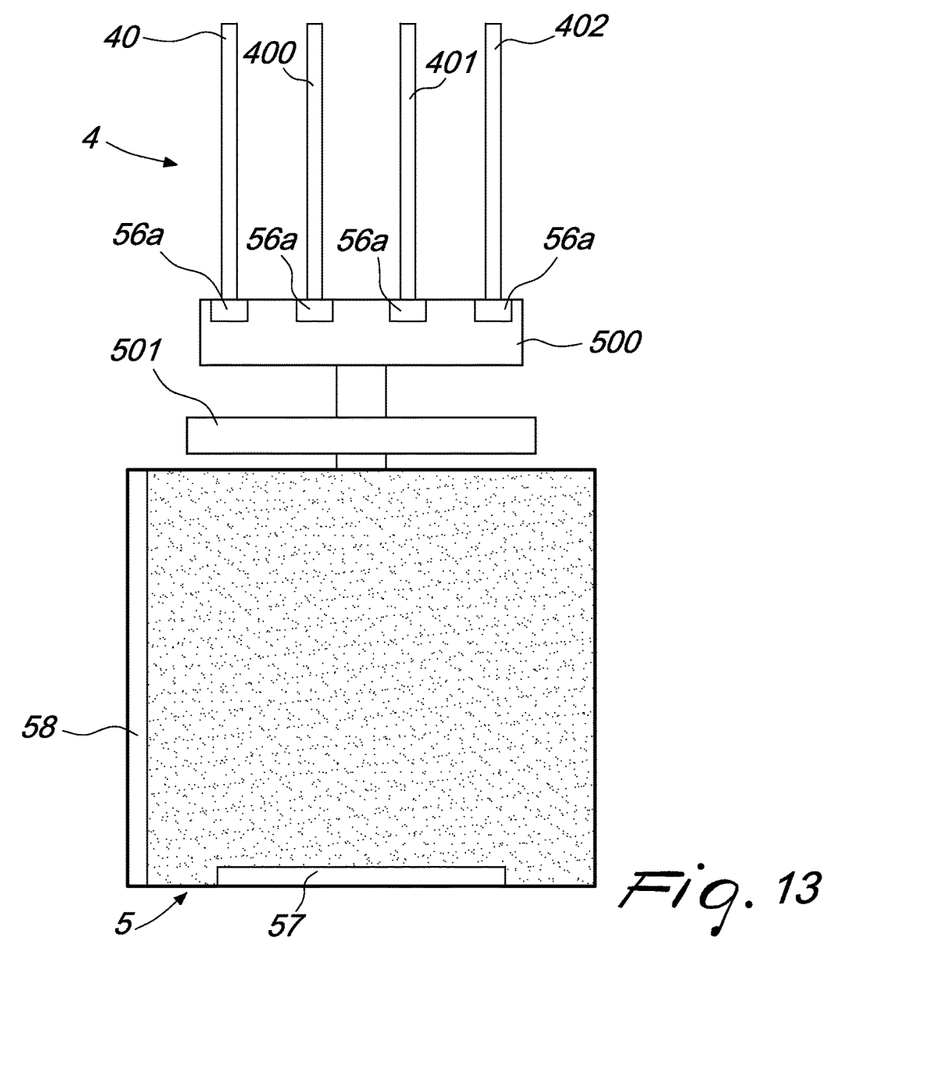
FIG. 13 is a view from above of a part of the diagnostic device in FIG. 1, illustrating in particular a second variation of the interface between the separation station and the electrophoresis chamber.

According to a second variation of the interface between the filtration station 4 and the electrophoresis chamber 5, shown in FIG. 13, a further shut-off valve 501 is interposed between the collection well 500 and the electrophoresis chamber 5. The shut-off valve 501 is adapted to be open when the electrical fields are activated in order to execute the electrophoresis. The presence of the shut-off valve 501 is particularly useful for electrophoretic gels with low retentive capacity, which tend to dehydrate on prolonged contact with air, thus damaging the functionality of the diagnostic device 1.

All the structures of chambers and capillary ducts are provided in a single chip 10 by way of electronic lithography techniques. The chip 10 can be provided starting from one or more superimposed wafers 100, 101. Chambers and ducts can be provided advantageously in the semiconductor material of the chip 10 by way of vertical etching, or other conventional methods in the sector.

Advantageously, furthermore, one or more of the capillary ducts that are present in the diagnostic device 1 can be provided with pumps 33 that are adapted to favor the flow of the fluid within the ducts, such as, for example, capillary pumps. By way of example, the accompanying figures schematically illustrate the capillary pump 33, which is arranged at the main capillary duct 30, proximate to the discharge chamber 9, and the capillary pump 53, which is arranged at the second capillary duct 50, proximate to the reaction chamber 6.

Figure 14:
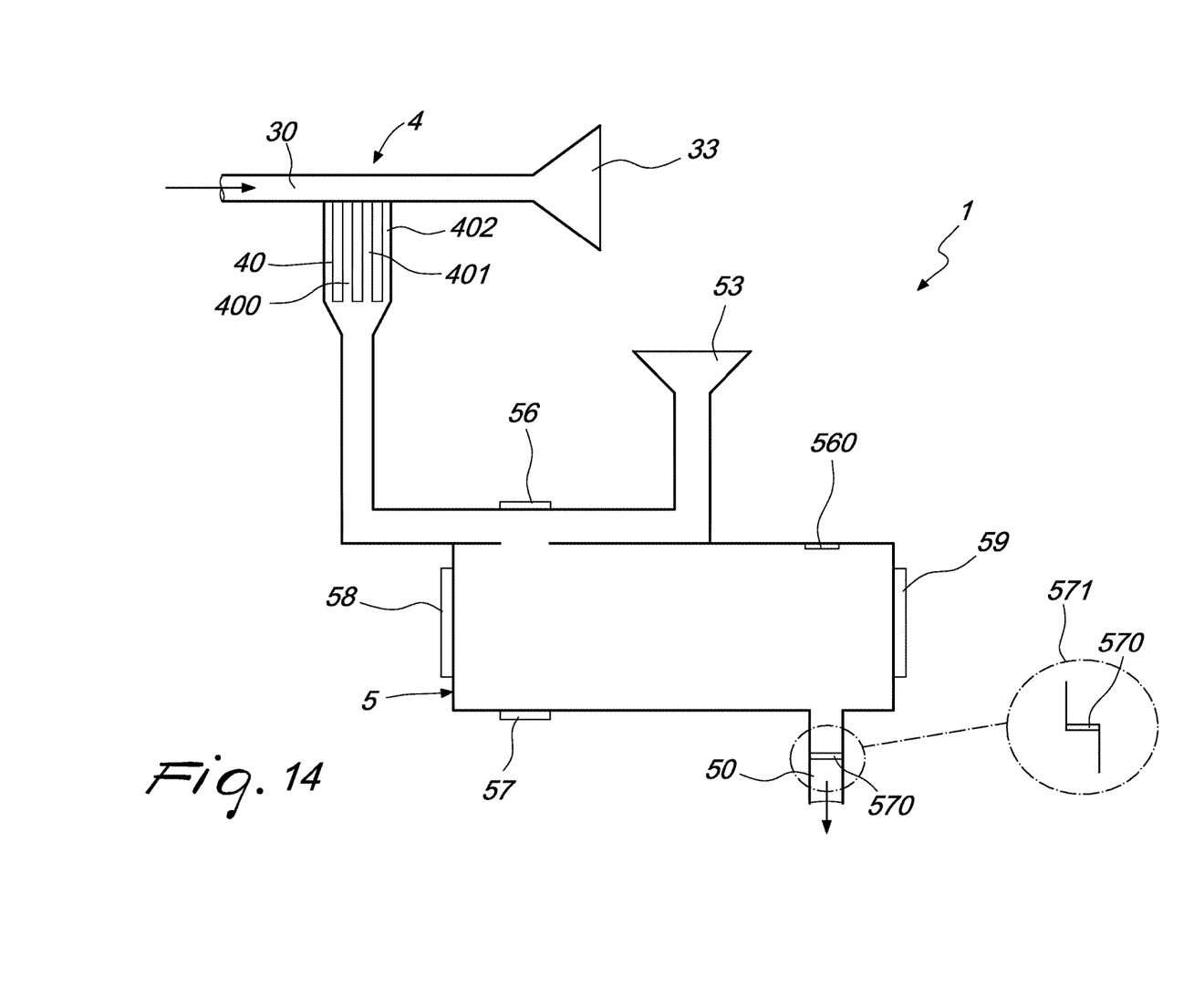
FIG. 14 is a view from above of a portion of a variation of the diagnostic device in FIG. 1.

In particular, FIG. 14 illustrates a variation of the device 1, which uses the capillary pumps 33 and 53, which are suitable for fluids that have circulating problems by simple capillary action. Further conventional pumps can be used in order to ensure the circulation of particularly difficult fluids. The electrophoresis chamber 5 can comprise two further electrodes 560 and 570, which are advantageously arranged in axial alignment with the second capillary duct 50. Advantageously the second capillary duct 50, which is substantially at the placement of the electrode 570, can have, in cross-section, a stepped configuration. Such stepped configuration is shown in cross-section, by way of example, in the inset 571 in FIG. 14.

Operation of the diagnostic device 1, particularly for a lab-on-chip, is clear and evident from the foregoing description.

The method of detection of a target in a native sample of a fluid to be tested is briefly summarized below:

First of all the native sample of fluid is introduced directly into the insertion station 2, and proceeds to the stabilization chamber 3, where it is stabilized in order to prevent possible deterioration effects and in order to optimize the pH level. By way of the separation station 4 the sample is filtered of corpuscles and potentially bothersome chemicals, such as cells and lipids. In passing through the electrophoresis chamber 5, the solution with the target is separated by electrophoresis and purified, so that the target can reach the reaction chamber 6. In the reaction chamber 6 the assay for detection is obtained by way of interaction with an adapted reagent solution for detection, for example, in the specific case of a protein target, with a specific antibody, or with other reagent solutions for the detection of non-proteic targets such as, for example, mRNA, DNA, ionic molecules and the like.

In particular, with a view to the stabilization of the diagnostic device 1 for the long-term storage thereof a dynamic assay is employed, in that the reaction chamber 6 is subdivided by the valve 62 into at least two chambers, the first chamber 60 containing the solution to be tested, and the second chamber 61 containing the reference solution. In fact only when the solution to be tested completely fills the first chamber 60 will the valve 62 open in order to allow the solution to be tested to be mixed with the reference solution and thus give rise to the reaction to be monitored. For the detection of such reaction, according to the characteristics of the target to be analyzed, two conventional types of detection are provided, i.e. calorimetric detection or interferometric detection.

The detection step is generally followed by the blank test step.

Capillary pressure is the motor that makes it possible for the sample to move in the circuit, as long as the air contained in the circuit itself is able to conveniently compress and expand in order to prevent the capillary pressure from being insufficient to enable the movement of the sample.

In practice it has been found that the diagnostic device, particularly of the lab-on-chip type, according to the present disclosure achieves the intended aim and objects in that it ensures a greater and better manageability.

In particular, the diagnostic device, according to the disclosure, makes it possible to directly analyze the native sample taken without the need for preliminary treatments, given that all the operations necessary to the detection of the target, from stabilization to purification, occur directly in the device itself, which is provided in a single chip.

Furthermore, the diagnostic device according to the disclosure does not require any particular activation of the surfaces through which the sample passes. In fact, during construction, assembly or use, no special processing of the surfaces is required in order to make them receptive to the various operations.

Moreover, the diagnostic device according to the disclosure can also easily include a blank chamber. In fact the blank test, i.e. a test on reagents that are quantitatively and qualitatively known, is indispensable in any experimental biological detection, in order to prevent the deterioration of the detection reagents, or the de-calibration of the detection system, from leading to potentially dangerous false positives. The fact that such test can be executed automatically in parallel with the reading of the sample analyzed in the chip itself ensures the homogeneity of the results, a time saving, and higher reliability of the measurement.

Another advantage of the diagnostic device, according to the disclosure, is that it ensures the preservability and unalterability of the sample and of the reference reagent solution.

Another advantage of the diagnostic device, according to the disclosure, is that it does not require fixing of the target and of the detection reagents, in that the isolation between the sections that define the device is provided directly by the electrophoretic gel contained in the electrophoresis chamber.

Another advantage of the diagnostic device, according to the disclosure, relates to the fact that the sample to be analyzed can be directly loaded in the chip, thus ensuring a higher level of accuracy in the collection of data and better reproducibility of the results.

Another advantage of the diagnostic device, according to the disclosure, is that it requires limited handling by the operating technician, thus reducing the usage time and limiting the risks of contamination of the sample by external agents.

Another advantage of the diagnostic device, according to the disclosure, relates to the fact that it can easily find application not only in the clinical sector, but also in the sector of biological, biochemical, pharmacological and immunological research, as well as in the industrial sector, for example in the food sector.

The diagnostic device, particularly of the lab-on-chip type, thus conceived is susceptible of numerous modifications and variations.

Moreover, all the details may be substituted by other, technically equivalent elements.

In practice the materials employed, provided they are compatible with the specific use, and the contingent dimensions and shapes, may be any according to requirements.

The disclosures in Italian Patent Application No. MI2013A001541 from which this application claims priority are incorporated herein by reference.

The invention claimed is:

1. A diagnostic device, particularly of the lab-on-chip type, comprising:
   an insertion station configured for inserting a native sample of a fluid to be tested;
   a stabilization chamber configured for stabilizing said native sample, directly connected to said insertion station;
   a separation station configured for separating said native sample, with a capillary connection to said stabilization chamber, said separation station comprising a main capillary duct and at least one lateral capillary duct that branches from said main capillary duct, an opening of said lateral capillary duct having a cross-section that is substantially smaller than the cross-section of an opening of said main capillary duct;
   an electrophoresis chamber, with a capillary connection to said separation station;
   a reaction chamber;
   at least one pair of electrodes which are arranged upstream and downstream of said electrophoresis chamber, an electrical field generated by said pair of electrodes propelling a sample from said electrophoresis chamber to said reaction chamber, a separative electrophoresis occurring inside said electrophoresis chamber;
   said insertion station, said stabilization chamber, said separation station, said electrophoresis chamber and said reaction chamber being defined in a single chip and comprising inert containment surfaces, said diagnostic device comprising a blank solution chamber, adapted to contain a blank solution, said blank solution chamber being connected to said reaction chamber by way of a first valve, wherein said at least one lateral capillary duct comprises at least one longitudinal portion that has a transverse cross-section of greater area than a transverse cross-section of the remaining longitudinal portion of said lateral capillary duct, said longitudinal portion having a transverse cross-section of greater area defining a first expansion volume.

2. The diagnostic device according to claim 1, further comprising, between said electrophoresis chamber and said reaction chamber, a second capillary duct that is extended longitudinally, said second capillary duct comprising at least one longitudinal portion that has a transverse cross-section of greater area than a transverse cross-section of a remaining longitudinal portion of said second capillary duct, said longitudinal portion having a transverse cross-section of greater area defining a second expansion volume.

3. The diagnostic device according to claim 1, wherein said reaction chamber comprises a first chamber, which is adapted to contain the solution to be tested, and a second chamber, which is adapted to contain a reagent solution, said first chamber and said second chamber being separated by a second valve.

4. The diagnostic device according to claim 3, wherein said reaction chamber comprises said blank solution chamber, said reaction chamber comprising a third valve that is adapted to separate said second chamber into two sub-chambers, the first sub-chamber being connected to said first chamber by way of said second valve, the second sub-chamber being connected to said blank solution chamber by way of said first valve.

5. The diagnostic device according to claim 1, further comprising a discharge chamber, which has a capillary connection to said stabilization chamber, and is adapted to collect the waste filtered by said separation station.

6. The diagnostic device according to claim 1, further comprising an overflow chamber adapted to collect an excess sample that exits from said stabilization chamber.

7. The diagnostic device according to claim 1, wherein said insertion station comprises a funnel-like element.

8. The diagnostic device according to claim 1, wherein one of said electrodes is arranged inside said reaction chamber.

* * * * *